United States Patent [19]

Rusay

[11] 4,277,500

[45] Jul. 7, 1981

[54] CERTAIN 2-HYDROXY-1-NAPHTHALDEHYDE ACYLHYDRAZONES AND THEIR USE AS FUNGICIDES

[75] Inventor: Ronald J. Rusay, Lafayette, Calif.

[73] Assignee: Stauffer Chemical Company, Westport, Conn.

[21] Appl. No.: 132,957

[22] Filed: Mar. 24, 1980

[51] Int. Cl.³ .................. A01N 37/18; C07C 103/20; C07C 103/56; C07C 103/75

[52] U.S. Cl. .................................. 424/324; 564/149; 564/150; 564/151

[58] Field of Search ............... 260/562 H, 558 H; 424/324; 564/149, 150, 151

[56] References Cited

U.S. PATENT DOCUMENTS

T857,036  12/1968  Straley et al. .................. 564/150
3,746,703  7/1973  Bruce ........................... 260/562 H Primary Examiner—Allen J. Robinson
Attorney, Agent, or Firm—Edwin H. Baker

[57] ABSTRACT

Certain 2-hydroxy-1-naphthaldehyde acylhydrazones which have the structural formula

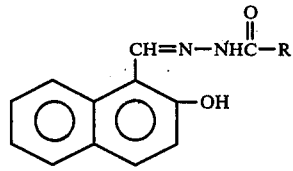

where R is phenyl, hydroxyphenyl, alkyl $C_1$–$C_4$, benzyl or halophenyl and their uses as a fungicide.

6 Claims, No Drawings

CERTAIN 2-HYDROXY-1-NAPHTHALDEHYDE ACYLHYDRAZONES AND THEIR USE AS FUNGICIDES

BACKGROUND OF THE INVENTION

This invention relates to certain 2-hydroxy-1-naphthaldehyde acylhydrazones which are useful as fungicides.

DESCRIPTION OF THE INVENTION

The compounds of the present invention are certain 2-hydroxy-1-naphthaldehyde acylhydrazones and have the following structural formula

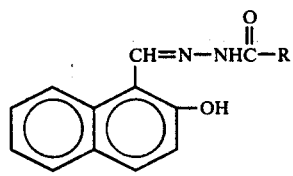

where R is phenyl; hydroxyphenyl, preferably 2-hydroxyphenyl; alkyl $C_1$-$C_4$, preferably methyl; benzyl; halophenyl, preferably dihalophenyl, more preferably 2,4-dihalophenyl.

In the above description of the compounds of this invention, alkyl includes both straight chain and branched chain configurations, for example, methyl, ethyl, n-propyl, isopropyl, n-butyl, sec-butyl or tert. butyl. The term halo includes chlorine, bromine, iodine and fluorine.

The compounds of the present invention can be prepared by the following general method.

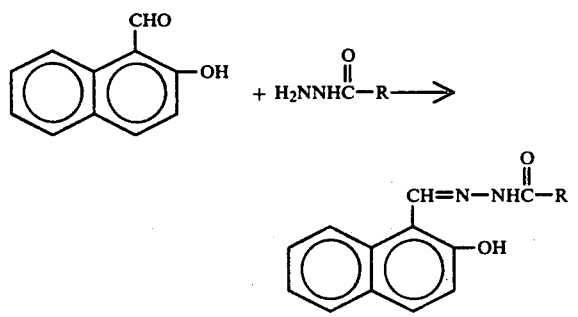

Generally, equimolar amounts of aldehyde and hydrazide are mixed in an appropriate solvent, such as toluene and the reaction mixture refluxed until water is no longer azeotropically removed. The mixture is cooled, filtered, and the filtrate washed with fresh reaction solvent.

Preparation of the compounds of this invention is illustrated by the following example.

EXAMPLE I

2-Hydroxy-1-naphthaldehyde salicyl hydrazone

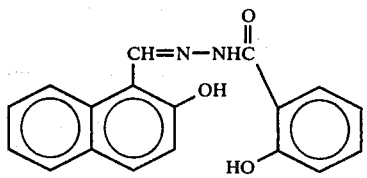

Firstly, 3.04 grams (20 millimoles) of salicyl hydrazide is added to 3.44 grams (20 millimoles) of 2-hydroxy-1-naphthaldehyde in 150 milliliters of toluene in a 300 milliliter flask equipped with a magnetic stirring bar and a Dean Stark trap. The reaction mixture is then heated to reflux temperature, and after azeotropic removal of water has ceased, cooled to ambient temperature. The solid product is filtered and washed twice with 20 milliliters of toluene to produce 3.54 grams (58%) of the desired compound.

The following is a table of certain selected compounds that are preparable according to the procedure described hereto. Compound numbers are assigned to each compound and are used throughout the remainder of the application.

TABLE I

| Compound Number | R | Melting Point |
|---|---|---|
| 1 | 2-hydroxyphenyl (OH) | 261–263° C. |
| 2 | phenyl | 212–213° C. |
| 3 | $CH_3$— | 230–240° C. |
| 4 | n-$C_3H_7$— | 155–156° C. |
| 5 | 2,4-dichlorophenyl (Cl, Cl) | 227–228° C. |
| 6 | benzyl (phenyl-$CH_2$—) | 190–192° C. |

Foliar Fungicide Evaluation Tests

A. Evaluation for Preventive Action

1. Bean Rust Test

Pinto bean plants (*Phaseolus vulgaris* L.) approximately 10 centimeters tall are transplanted into sandy loam soil in three-inch clay pots. The plants are then inverted and dipped for two to three seconds in 50—50 acetone water solution of the test chemical. Test concentrations range from 1000 ppm downward. After the leaves are dried, they are inoculated with a water suspension of spores of the bean rust fungus (*Uromyces phaseoli* Arthur) and the plants are placed in an environment of 100% humidity for 24 hours. The plants are then removed from the humidity chamber and held until disease pustules appear on the leaves. Effectiveness is recorded as the lowest concentration, in ppm, which will provide 75% or greater reduction in pustule formation as compared to untreated, inoculated plants. These values are recorded in Table II.

2. Tomato Early Blight

A candidate compound is dissolved in an appropriate solvent and diluted with a 50—50 acetone water solution. Four week old tomato (*Lycopersicon esculentum*) plants are then sprayed with the solution to the point of runoff. Test concentrations range from 1000 ppm downward. When the leaves are dry, they are inoculated with a water suspension of spores of the early blight fungus (*Alternaria solani* Ellis and Martin) and placed in an environment of 100% humidity for 48 hours. The plants are then removed from the humidity chamber and held until disease lesions appear on the leaves. Effectiveness is recorded as the lowest concentration, in ppm, which will provide 75% or greater reduction in number of lesions formed as compared to untreated, inoculated plants. These values are recorded in Table II.

TABLE II

| | Preventive Action | |
|---|---|---|
| Compound Number | Bean Rust | Tomato Early Blight |
| 1 | 100 | 5 |
| 2 | 1000 | * |
| 3 | 1000 | * |
| 4 | 1000 | * |
| 5 | 1000 | * |
| 6 | 1000 | * |

*Not active at 1000 ppm and not tested at a higher concentration

The compounds of this invention are generally embodied into a form suitable for convenient application. For example, the compounds can be embodied into a pesticidal composition which is provided in the form of emulsions, suspensions, solutions, dusts and aerosol sprays. In general, such compositions will contain, in addition to the active compound, the adjuvants which are found normally in pesticide preparations. In these compositions, an active compound of this invention can be employed as the sole pesticide component or it can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays, propellants, such as dichlorodifluoromethane, etc. If desired, however, an active compound can be applied directly where control is desired.

The precise manner in which the pesticidal compositions of this invention are used in any particular instance will be readily apparent to a person skilled in the art. The concentration of the active compound in the present compositions can vary within rather wide limits, ordinarily the compound will comprise not more than about 15.0% by weight of the composition. Preferably, however, the pesticide compositions of this invention will be in the form of a solution or suspension containing up to about 1.0% by weight of the active pesticide compound.

I claim:

1. Compounds having the following structural formula

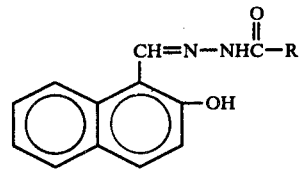

where R is phenyl; alkyl $C_1$–$C_4$; benzyl or halophenyl.

2. The compound of claim 1 wherein R is dihalophenyl.

3. The compound of claim 1 wherein R is 2,4-dihalophenyl.

4. The compound of claim 1 wherein R is 2,4-dichlorophenyl.

5. A method of controlling fungi comprising applying thereto a fungicidally effective amount of a compound having the following structural formula

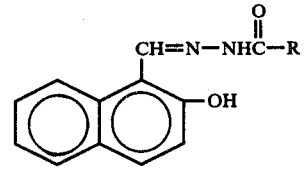

where R is phenyl; hydroxyphenyl; alkyl $C_1$–$C_4$; benzyl or halophenyl.

6. A fungicidal composition comprising a fungicidally effective amount of a compound having the following structural formula

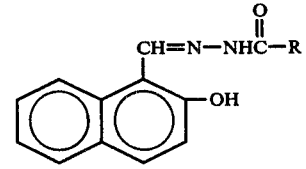

where R is phenyl; alkyl $C_1$–$C_4$; benzyl or halophenyl and an inert carrier.

* * * * *